United States Patent
Kimishima

(10) Patent No.: US 10,739,138 B2
(45) Date of Patent: Aug. 11, 2020

(54) INFORMATION PROCESSING APPARATUS AND CONTROL METHOD

(71) Applicant: SONY CORPORATION, Tokyo (JP)

(72) Inventor: Masato Kimishima, Tokyo (JP)

(73) Assignee: SONY CORPORATION, Tokyo (JP)

( * ) Notice: Subject to any disclaimer, the term of this patent is extended or adjusted under 35 U.S.C. 154(b) by 308 days.

(21) Appl. No.: 15/579,637

(22) PCT Filed: Apr. 28, 2016

(86) PCT No.: PCT/JP2016/063328
§ 371 (c)(1),
(2) Date: Dec. 5, 2017

(87) PCT Pub. No.: WO2016/203857
PCT Pub. Date: Dec. 22, 2016

(65) Prior Publication Data
US 2018/0156620 A1    Jun. 7, 2018

(30) Foreign Application Priority Data

Jun. 15, 2015 (JP) ................................ 2015-120520

(51) Int. Cl.
*G01C 21/16* (2006.01)
*G01S 19/34* (2010.01)
(Continued)

(52) U.S. Cl.
CPC ............. *G01C 21/16* (2013.01); *G01C 21/10* (2013.01); *G01C 21/12* (2013.01); *G01C 21/20* (2013.01);
(Continued)

(58) Field of Classification Search
CPC ........ G01C 21/16; G01C 21/12; G01C 25/00; G01C 21/10; G01C 21/20; G01C 22/006;
(Continued)

(56) References Cited

U.S. PATENT DOCUMENTS 5,905,460 A * 5/1999 Odagiri et al. ......... G01S 19/34
701/491
5,982,324 A * 11/1999 Watters et al. ......... G01S 19/34
701/469
(Continued)

FOREIGN PATENT DOCUMENTS

CN    103765161 A    4/2014
CN    103852768 A    6/2014
(Continued)

OTHER PUBLICATIONS

International Search Report and Written Opinion of PCT Application No. PCT/JP2016/063328, dated May 31, 2016, 9 pages of ISRWO.

*Primary Examiner* — Dale W Hilgendorf
(74) *Attorney, Agent, or Firm* — Chip Law Group

(57) ABSTRACT

An information processing apparatus includes a distance calculation unit to calculate a moving distance of a user by using an absolute position of the user measured by an absolute positioning unit and a control unit to perform control to turn off the absolute positioning unit in a case where the moving distance becomes a predetermined distance.

13 Claims, 11 Drawing Sheets

(51) Int. Cl.

| | |
|---|---|
| *G01C 21/12* | (2006.01) |
| *G01C 25/00* | (2006.01) |
| *G01C 21/28* | (2006.01) |
| *G01C 21/10* | (2006.01) |
| *G01C 21/20* | (2006.01) |
| *G01C 22/00* | (2006.01) |
| *A61B 5/11* | (2006.01) |
| *G01S 19/48* | (2010.01) |

(52) U.S. Cl.
CPC ........... *G01C 21/28* (2013.01); *G01C 22/006* (2013.01); *G01C 25/00* (2013.01); *G01S 19/34* (2013.01); *A61B 5/112* (2013.01); *A61B 2560/0209* (2013.01); *A61B 2562/0219* (2013.01); *G01S 19/48* (2013.01)

(58) Field of Classification Search
CPC ......... G01C 21/28; G01S 19/34; G01S 19/48; A61B 5/112; A61B 2560/0209; A61B 2562/0219
See application file for complete search history.

(56) References Cited

U.S. PATENT DOCUMENTS

| | | | | |
|---|---|---|---|---|
| 6,132,397 A | * | 10/2000 | Onari et al. ......... | G01C 22/006 600/595 |
| 6,204,807 B1 | * | 3/2001 | Odagiri et al. ......... | G01S 19/34 701/469 |
| 6,546,336 B1 | * | 4/2003 | Matsuoka et al. ... | G01C 22/006 701/472 |
| 6,898,521 B2 | * | 5/2005 | Yanai ................... | G01C 21/362 701/414 |
| 8,417,265 B2 | * | 4/2013 | Kimishima ............ | G01C 17/38 701/491 |
| 8,903,418 B2 | * | 12/2014 | Fukumoto et al. ..... | G01S 19/48 455/574 |
| 10,401,504 B2 | * | 9/2019 | Sugiyama et al. ....... | G01S 19/34 |
| 2012/0215442 A1 | * | 8/2012 | Sambongi ............ | G01C 22/006 701/472 |
| 2013/0138394 A1 | * | 5/2013 | Shiga ................... | G01C 22/006 702/160 |
| 2014/0163871 A1 | * | 6/2014 | Shingyoji ............ | G01C 22/006 701/490 |
| 2014/0180626 A1 | * | 6/2014 | Kimishima ............ | G01S 19/49 702/142 |

FOREIGN PATENT DOCUMENTS

| | | |
|---|---|---|
| JP | 11-132786 A | 5/1999 |
| JP | 2013-050307 A | 3/2013 |
| JP | 2014-115093 A | 6/2014 |
| WO | 2013/031355 A1 | 3/2013 |

* cited by examiner

INFORMATION PROCESSING APPARATUS AND CONTROL METHOD

CROSS REFERENCE TO RELATED APPLICATIONS

This application is a U.S. National Phase of International Patent Application No. PCT/JP2016/063328 filed on Apr. 28, 2016, which claims priority benefit of Japanese Patent Application No. JP 2015-120520 filed in the Japan Patent Office on Jun. 15, 2015. Each of the above-referenced applications is hereby incorporated herein by reference in its entirety.

TECHNICAL FIELD

The present disclosure relates to an information processing apparatus, a control method, and a program.

BACKGROUND ART

In recent years, a system using position information has been widely diffused. As a method of acquiring position information, for example, absolute positioning such as a global positioning system (GPS) positioning or WiFi (registered trademark) is used. By causing GPS capable of acquiring position information of an individual user to be always on, a moving position, a moving distance, and a moving speed are continuously acquired and are used when feedback is provided to the user in a running application, a walking application, or the like.

Further, as the method of acquiring position information, it is also possible to use autonomous positioning that obtains current position information by calculating a relative position from the last positioning spot obtained by absolute positioning on the basis of information acquired by a sensor or the like. For example, Patent Literature 1 cited below discloses a technology of further improving accuracy of a correspondence table (which is a correspondence table of a walking pace and a step length and is used to calculate speed) used for autonomous positioning at the time of walking.

CITATION LIST

Patent Literature

Patent Literature 1: JP 2013-50307A

DISCLOSURE OF INVENTION

Technical Problem

However, absolute positioning using GPS or the like has high accuracy but consumes a large amount of power, whereas the above-mentioned autonomous positioning consumes a remarkably low amount of power but is problematic in that accuracy is low in a case where learning is not satisfactorily performed.

Further, it is possible to consider a method of turning on/off absolute positioning using GPS or the like at certain time intervals and calculating speed by measuring a walking pitch while the absolute positioning is off. However, whether or not learning accuracy is satisfactory is not secured even in a case where a certain time elapses.

In view of this, the present disclosure proposes an information processing apparatus, a control method, and a program capable of improving accuracy of autonomous distance measurement by turning off absolute positioning in accordance with a moving distance.

Solution to Problem

According to the present disclosure, an information processing apparatus including: a distance calculation unit configured to calculate a moving distance of a user by using an absolute position of the user measured by an absolute positioning unit; and a control unit configured to perform control to turn off the absolute positioning unit in a case where the moving distance becomes a predetermined distance.

According to the present disclosure, there is provided an information process method including causing a processor to calculate a moving distance of a user by using an absolute position of the user measured by an absolute positioning unit, and perform control to turn off the absolute positioning unit in a case where the moving distance becomes a predetermined distance.

According to the present disclosure, there is provided a program for causing a computer to function as a distance calculation unit configured to calculate a moving distance of a user by using an absolute position of the user measured by an absolute positioning unit, and a control unit configured to perform control to turn off the absolute positioning unit in a case where the moving distance becomes a predetermined distance.

Advantageous Effects of Invention

As described above, according to the present disclosure, it is possible to improve accuracy of autonomous distance measurement by turning off absolute positioning in accordance with a moving distance.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
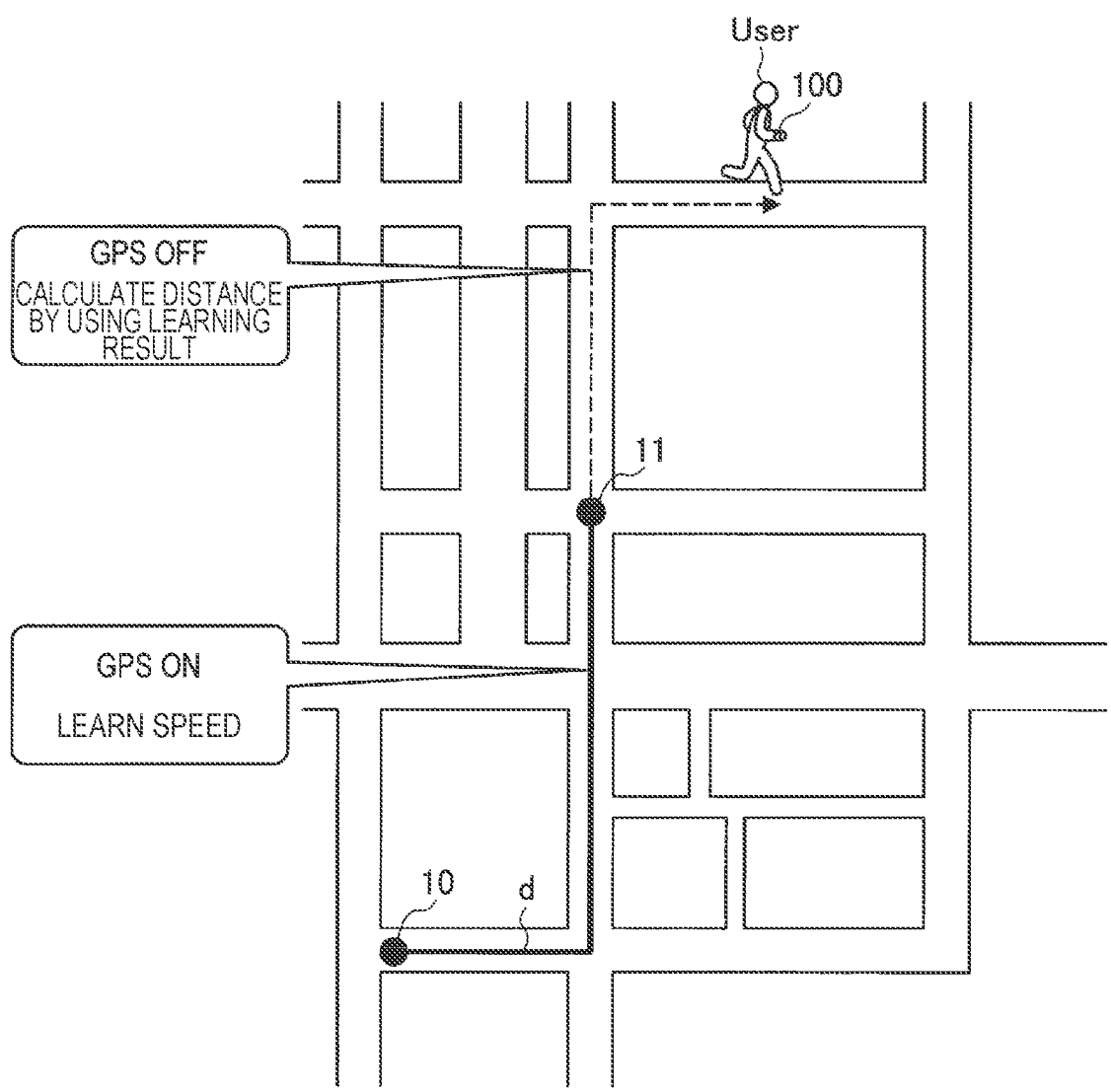
FIG. 1 is a view for describing an outline of a control system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Further, description will be provided in the following order.

1. Outline of control system according to embodiment of present disclosure
2. First embodiment
2-1. Functional configuration example
2-2. Hardware configuration example
2-3. Operation example
2-4. Modification example
3. Second embodiment
4. Third embodiment
4-1. Functional configuration example
4-2. Operation example
5. Conclusion

1. Outline of Control System According to Embodiment of Present Disclosure

First, an outline of a control system according to an embodiment of the present disclosure will be described. For example, in an information processing apparatus such as a navigation apparatus, a terminal device having a function of acquiring position information has been diffused. A method of acquiring position information in this information processing apparatus is, for example, absolute positioning using a positioning satellite such as GPS and absolute positioning of calculating a current position by estimating, on the basis of reception strengths of Wifi electric waves from Wifi base stations, a distance from each of the base stations. A user can recognize a walking distance or a running distance in real time by carrying an information processing apparatus having an absolute positioning function in a case where the user is walking or running. The information processing apparatus can calculate a moving distance of the user on the basis of absolute position information that has been continuously or regularly acquired and display the calculated moving distance on a display unit of the information processing apparatus.

However, absolute positioning using a positioning satellite such as GPS is problematic in that power consumption is high. Herein, as a method of calculating a moving distance without using position information, there is autonomous positioning that obtains current position information by calculating a relative position from the last positioning spot obtained by absolute positioning on the basis of information acquired by a sensor or the like. Patent Literature 1 cited above discloses a technology of performing learning for autonomous positioning (generation of a correspondence table of a walking pace and a step length) while GPS is on and performing autonomous positioning by using a learning result in a case where positioning using GPS cannot be performed (for example, in a case of moving into a building). Specifically, the number of steps is counted to calculate a walking pace, and a step length (k) corresponding to the walking pace (f: the number of steps per unit time) is acquired from a correspondence table, and therefore a moving speed (v=k×f) is acquired. However, GPS is always on while positioning using GPS can be performed, and therefore power consumption is high as described above. Further, it is considered that GPS is turned on/off at certain time intervals and learning is performed while GPS is on, whereas autonomous positioning is performed by using the learning result while GPS is off. However, whether or not learning accuracy is satisfactory when the GPS is turned off after a certain time is not secured. For example, it is also expected that, even in a case where a certain time elapses, the user hardly moves and learning of a step length and a walking pace is not satisfactorily performed. In this case, an error occurs at the time of calculating speed (see FIG. 2 described below).

In view of this, in the control system according to the present embodiment, it is possible to perform absolute positioning operation necessary and sufficient to secure learning accuracy by turning off absolute positioning using GPS or the like in accordance with a moving distance. With this, it is possible to minimize absolute positioning operation to thereby cut power consumption and secure learning accuracy to thereby continue highly accurate distance calculation (autonomous distance measurement) and position measurement (autonomous positioning) for a long time. Herein, FIG. 1 is a view for describing an outline of a control system according to an embodiment of the present disclosure. Note that, in the present specification, description will be provided below by using GPS as an example of an absolute positioning unit.

As shown in FIG. 1, for example, in a case where the user is running while carrying an information processing apparatus 100, GPS provided in the information processing apparatus 100 is controlled to be on from a start spot 10 to a movement spot 11 located at a certain distance d therefrom and a distance is calculated on the basis of position information acquired by the GPS. Further, a walking pitch (the number of steps per unit time) is learned during this time.

Then, the GPS is controlled to be off from the movement spot 11 by using the user having moved the certain distance d as a trigger, and a moving distance is calculated on the basis of, for example, a walking pitch acquired by an acceleration sensor and a learning result that has been obtained while the GPS has been controlled to be on.

As described above, in the control system according to the present embodiment, off control of the GPS is performed by using movement of the certain distance d as a trigger, and a moving distance is calculated by using a learning result after the GPS is turned off, and therefore it is possible to cut power consumption and secure learning accuracy. Such an effect of securing learning accuracy in the present embodiment will be described with reference to FIG. 2.

Figure 2:
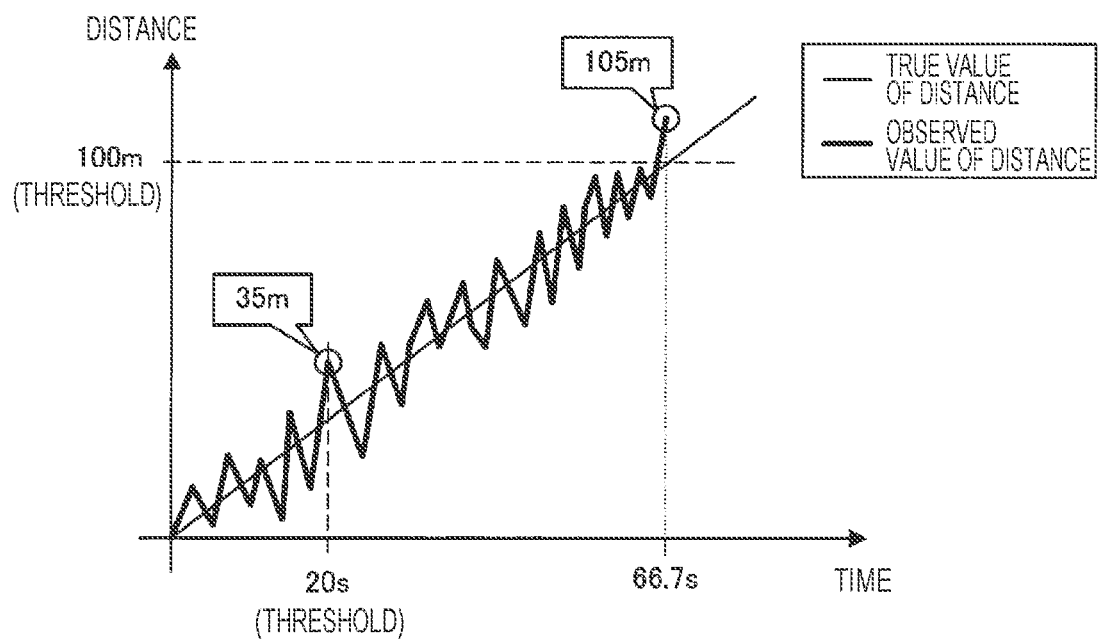
FIG. 2 is a view for describing a difference from a comparison example as to securing learning accuracy in the control system according to the present embodiment.

FIG. 2 is a view for describing a difference from a comparison example as to securing learning accuracy in the control system according to the present embodiment. For example, in learning a walking pitch when the GPS is on, a correlation between speed (m/sec) and walking pitch (step/sec) is specifically learned. The speed (m/sec) is calculated on the basis of a moving distance per unit time, and the moving distance is acquired on the basis of position information acquired by the GPS. A graph in FIG. 2 shows a true value of a distance and an observed value of the distance acquired on the basis of position information obtained by the GPS. Herein, an error occurs in absolute position measurement using the GPS, which influences the observed value of the distance. For example, it is assumed that a positional error of the GPS is 5 m at a maximum, an error of a distance to be observed is 5 m at a maximum, and this maximum value of 5 m is observed. Further, as an example, a positioning interval of the GPS is discontinuous and positioning is performed at intervals of, for example, 1 sec. Further, a true value of speed is assumed to be slightly low, i.e., to be 1.5 m/s as an example.

At this time, in a case of a comparison example where speed is learned at certain time (for example, 20 sec) intervals, as shown in FIG. 2, the observed value of the distance is 35 m (including the error of 5 m), and the speed (m/s) is calculated as follows: "35 m/20 s=1.75 m/s", which is an error of +16% with respect to the true value of the speed (1.5 m/s).

Meanwhile, in a case of the present embodiment in which speed is learned at certain distance (for example, 100 m) intervals, as shown in FIG. 2, the observed value of the distance is 105 m (including the error of 5 m), and the speed (m/s) is calculated as follows: "105 m/66.7 s=1.57 m/s", which is an error of +5% with respect to the true value of the speed (1.5 m/s).

As a result, an error occurring in learning of speed using a distance threshold is smaller than an error occurring in learning of speed using a time threshold. That is, in a case where speed is learned by using a time threshold, speed is calculated regardless of a total distance, and therefore, for example, in a case where the speed is low, a positional error of the GPS is relatively increased. This appears as a speed error. Therefore, it can be said that learning accuracy can be secured by learning speed by using a distance threshold, as compared with a case of learning speed by using a time threshold.

2. First Embodiment 2-1. Functional Configuration

Figure 3:
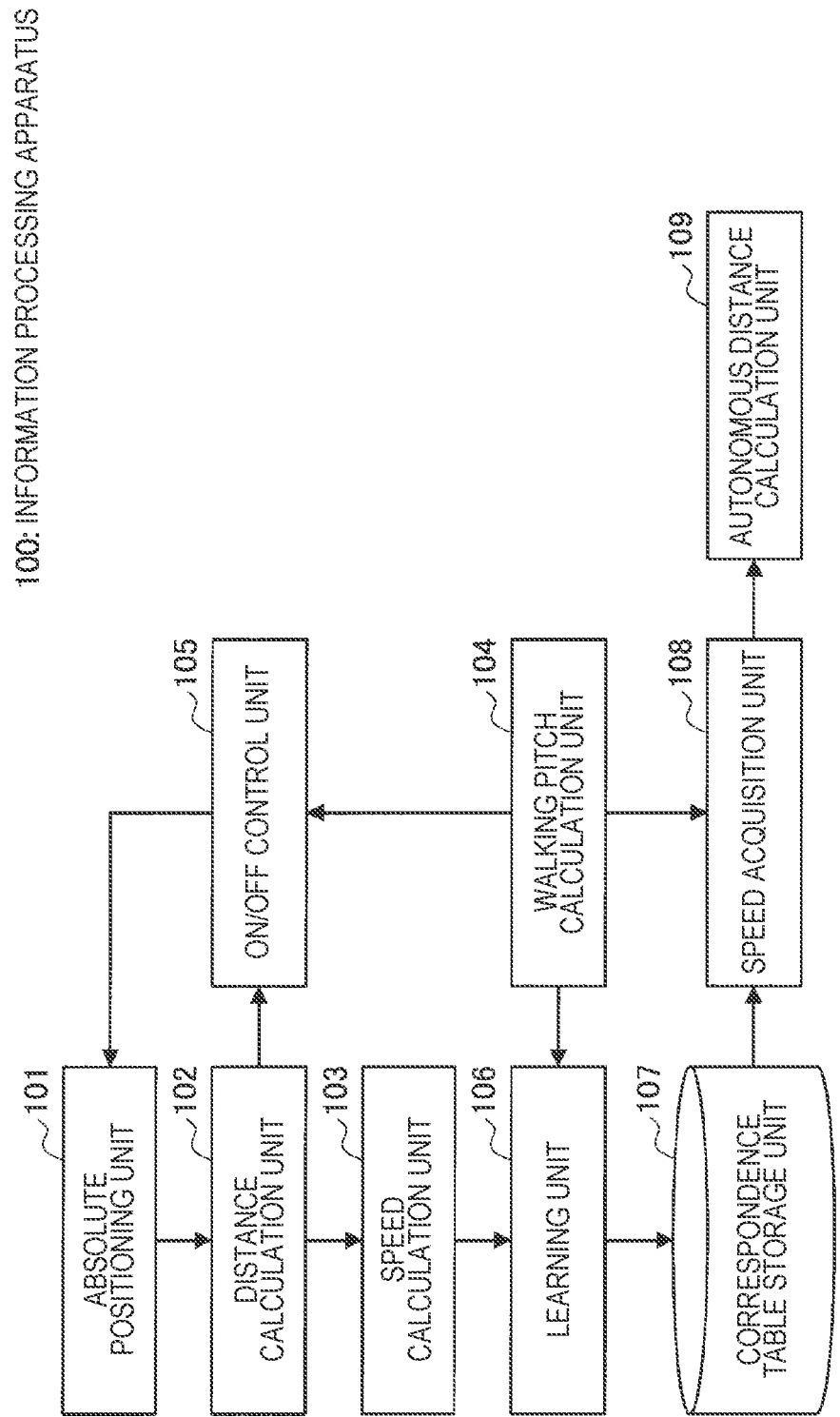
FIG. 3 is a block diagram showing a functional configuration of an information processing apparatus according to a first embodiment of the present disclosure.

Next, a functional configuration of the information processing apparatus 100 according to the first embodiment of the present disclosure will be described with reference to FIG. 3. FIG. 3 is a block diagram showing the functional configuration of the information processing apparatus 100 according to the first embodiment of the present disclosure.

The information processing apparatus 100 has a function of autonomously calculating a distance at the time of walking or running. The information processing apparatus 100 may be, for example, a mobile phone, a personal digital assistant (PDA), a smartphone, a wearable device (smartwatch, smarteyeglass, smartband, smartneck, or the like), a portable music reproduction device, a portable video processing apparatus, a portable game console, a portable personal computer (PC) (including a notebook PC and a tablet PC), or a navigation apparatus including a personal navigation device (PND). Note that, in the following description of the present embodiment, a user who carries the information processing apparatus 100 will be simply referred to as "user".

As shown in FIG. 3, the information processing apparatus 100 mainly includes an absolute positioning unit 101, a distance calculation unit 102, a speed calculation unit 103, a walking pitch calculation unit 104, an on/off control unit 105, a learning unit 106, a correspondence table storage unit 107, a speed acquisition unit 108, and an autonomous distance calculation unit 109.

(Absolute Positioning Unit 101)

The absolute positioning unit 101 has a function of acquiring an absolute position of the user. The absolute positioning unit 101 may be, for example, a GPS antenna and a GPS processing unit for processing a GPS signal received by the GPS antenna. Alternatively, the absolute positioning unit 101 may be a position calculation unit that estimates, on the basis of a Wifi antenna for receiving Wifi electric waves from a plurality of base stations and reception strengths of the received Wifi electric waves, a distance from each of the base stations and calculates a current position on the basis of the principle of triangulation by using the distance from each base station and a position of each base station.

(Distance Calculation Unit 102)

The distance calculation unit 102 has a function of calculating a moving distance of the user. The distance calculation unit 102 calculates a moving distance from a start spot (moving start spot of the user) by using the absolute position of the user acquired by the absolute positioning unit 101. The start spot may be a spot where a trigger for starting moving distance calculation is input by the user. For example, in a case where the user starts running, the user turns on GPS and inputs a start instruction of moving distance calculation (specifically, for example, start of a running application and a tap on a start button).

(Speed Calculation Unit 103)

The speed calculation unit 103 has a function of calculating a moving speed of the user. The speed calculation unit 103 calculates a moving speed of the user on the basis of the moving distance calculated by the distance calculation unit 102 and an elapsed time from start of moving. The calculated moving speed is output to the learning unit 106.

(Walking Pitch Calculation Unit 104)

The walking pitch calculation unit 104 has a function of calculating a walking pitch (the number of steps per unit time: steps/s) of the user. The walking pitch can be calculated on the basis of the number of steps detected by using a sensor for detecting shaking, such as an acceleration sensor, and a moving time period. The calculated walking pitch is output to the learning unit 106. Further, because it is possible to determine walking by using the acceleration sensor, it is possible to calculate a walking pace more accurately by excluding a period of time in which the user stops from the above moving time period. Note that detection of the number of steps is not limited to acceleration data detected by the acceleration sensor and may be performed on the basis of, for example, gyro data detected by a gyro sensor or pressure data detected by a pressure sensor provided in a sole of a shoe.

(On/Off Control Unit 105)

The on/off control unit 105 has a function of controlling on/off of the absolute positioning unit 101. Specifically, in a case where the moving distance of the user calculated by the distance calculation unit 102 becomes a certain distance, the on/off control unit 105 performs control to turn off the absolute positioning unit 101. Further, in a case where a change in walking pitch obtained while the absolute positioning unit 101 is off from a walking pitch obtained at the time of the previous learning is equal to or greater than a certain level, the on/off control unit 105 performs control to turn on the absolute positioning unit 101.

Herein, the certain distance may be determined in advance in accordance with, for example, accuracy of the absolute positioning unit 101 or may be determined by a certain distance determination unit (not shown). The accuracy of the absolute positioning unit 101 is estimated on the basis of performance of the absolute positioning unit 101 itself or a current surrounding environment. For example, accuracy of absolute positioning using GPS is reduced in an environment in which the sky is covered such as a street of buildings, a place under a girder bridge, and forest. Meanwhile, the accuracy of the absolute positioning using GPS is improved in a residential area made up of stand-alone houses, a large park, and a wide road. It is possible to grasp an environment around a current position by using, for example, position information acquired by the absolute positioning unit 101 and map information and estimate accuracy of an absolute position in accordance with what kind of place the current position is. Alternatively, the accuracy thereof may be determined on the basis of another GPS accuracy index. For example, the accuracy of the GPS positioning is also changed depending on the number of satellites from which the GPS antenna receives GPS signals (the number of positioning satellites that can be acquired by the information processing apparatus 100), a GPS reception strength, and the like. Therefore, the certain distance may be determined on the basis of the number of acquirable positioning satellites and the GPS reception strength. Further, for example, in a case where the absolute positioning unit 101 calculates an absolute position on the basis of a reception strength of a Wifi electric wave, accuracy of the absolute position is changed depending on the number of base stations from which the absolute positioning unit 101 receives Wifi electric waves (the number of base stations seen from the information processing apparatus 100). Therefore, the certain distance may be determined by estimating the accuracy of the absolute position on the basis of the number of base stations seen from the information processing apparatus 100.

(Learning Unit 106)

Figure 4:
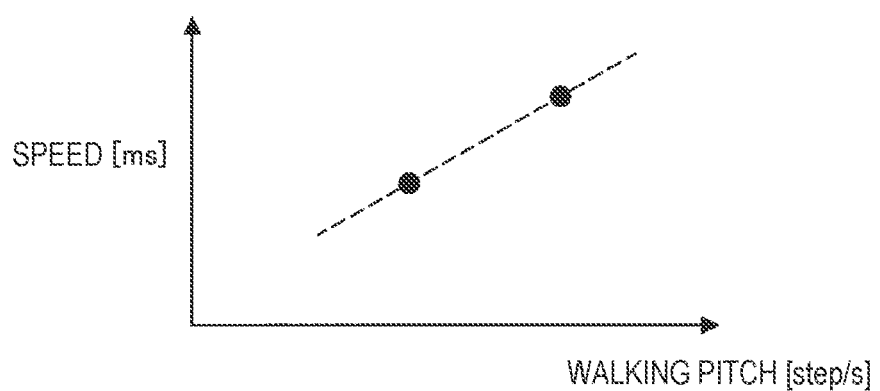
FIG. 4 is a view for describing learning of a correlation between speed and pitch according to the present embodiment.

The learning unit 106 has a function of learning correspondence (pair) between the speed calculated by the speed calculation unit 103 and the walking pitch calculated by the walking pitch calculation unit 104 while the absolute positioning unit 101 is on. For example, the learning unit 106 may continuously record speed and a walking pitch until the user moves a certain distance and learn average values thereof as a pair between the speed and the walking pitch. Further, the learning unit 106 can generate a correspondence table of the speed and the walking pitch and store the correspondence table on the correspondence table storage unit 107. Herein, FIG. 4 is a view for describing learning of a correlation between speed and pitch. The learning unit 106 learns a correlation between speed and pitch shown in FIG. 4. The correlation between speed and pitch is generally expressed by a linear equation, and therefore at least two points are necessary to perform accurate learning. That is, in a case of only a single point, only a y-intercept is determined and a default value is employed as an inclination, and therefore accuracy is reduced.

(Correspondence Table Storage Unit 107)

The correspondence table storage unit 107 has a function of storing the correspondence table generated by the learning unit 106. The correspondence table is, for example, information in which the moving speed (m/s) of the user calculated by the speed calculation unit 103 and a walking pitch (step/s) obtained when the moving speed is calculated are associated with each other.

Note that the correspondence table storage unit 107 is a device for storing data and can include a storage medium, a recording device for recording data on the storage medium, a reading device for reading data from the storage medium, a deletion device for deleting data recorded on the storage medium, and the like. Herein, the storage medium may be, for example, a nonvolatile memory such as a flash memory, a magnetoresistive random access memory (MRAM), a ferroelectric random access memory (FeRAM), a phase change random access memory (PRAM), and an electronically erasable and programmable read only memory (EEPROM) or a magnetic storage medium such as a hard disk drive (HDD).

(Speed Acquisition Unit 108)

The speed acquisition unit 108 has a function of, in a case where the absolute positioning unit 101 is off, referring to a speed correspondence table stored on the correspondence table storage unit 107 on the basis of the walking pitch calculated by the walking pitch calculation unit 104 and acquiring a current speed.

(Autonomous Distance Calculation Unit 109)

The autonomous distance calculation unit 109 is an autonomous distance measurement unit for calculating a moving distance of the user on the basis of the speed acquired by the speed acquisition unit 108 in a case where the absolute positioning unit 101 is off. For example, the autonomous distance calculation unit 109 can acquire a current walking pitch calculated by the walking pitch calculation unit 104 and speed associated with the walking pitch from a speed table and calculate a moving distance after the absolute positioning unit 101 is controlled to be off. As described above, in the present embodiment, even in a case where the absolute positioning unit 101 is off, it is possible to acquire speed and calculate a distance on the basis of a walking pitch measured by using the acceleration sensor and a learning result of speed.

Hereinabove, an example of the function of the information processing apparatus 100 according to the present embodiment has been described. The function of the information processing apparatus 100 according to the present embodiment is not limited to the example shown in FIG. 3 and may further include, for example, a navigation unit and a map information storage unit. The navigation unit has a function of showing the user a route to a predetermined spot from a current spot. Further, the map information storage unit has a function of storing map information. The map information stored herein may include, for example, not only landform data but also road network data and point of interest (POI) information.

Further, respective constituent elements described above may be configured using general-purpose members or circuits or may be configured using hardware specialized for the functions of the respective constituent elements. In addition, the functions of the respective constituent elements may be fulfilled by reading a control program from a storage medium such as a ROM (Read Only Memory) or a RAM (Random Access Memory) storing the control program describing procedures in which an arithmetic operation unit such as a CPU (Central Processing Unit) realizes the functions and by interpreting the program. Thus, it is possible to appropriately change a configuration to be used according to the level of the technology at a time when the present embodiment is implemented. Hereinbelow, an example of a hardware configuration to realize the function of the information processing apparatus 100 will be shown.

Note that a computer program for realizing each of the functions of the information processing apparatus 100 according to embodiments as described above may be created and installed in a personal computer, or the like. In addition, a recording medium that stores such a computer program and which is readable on the computer may also be provided. The recording medium may include, for example, a magnetic disk, an optical disc, a magneto optical disc, a flash memory, and the like. In addition, the computer program may be delivered through, for example, the Internet, without using the recording medium.

2-2. Hardware Configuration Example

Figure 5:
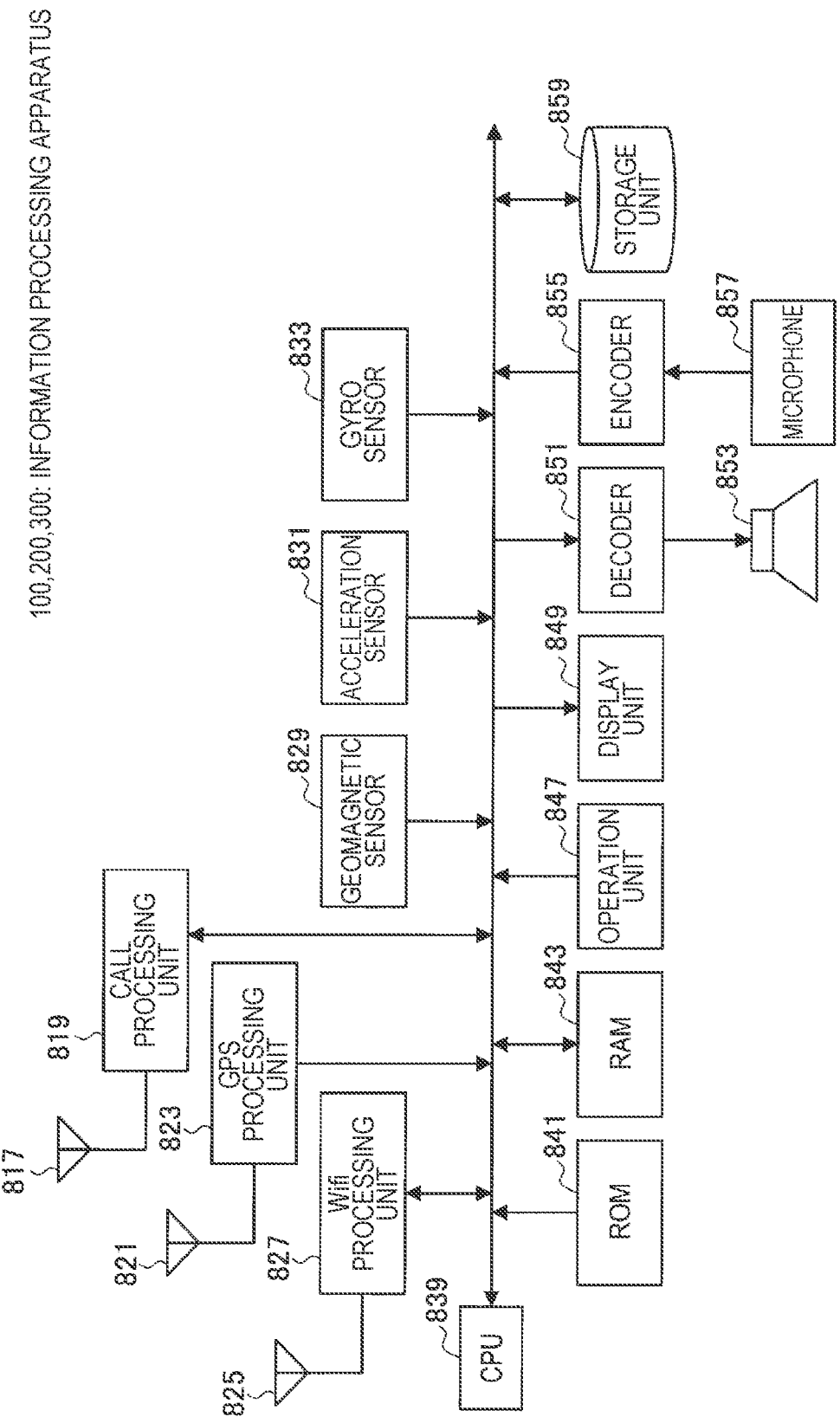
FIG. 5 is a block diagram showing a hardware configuration of an information processing apparatus according to an embodiment of the present disclosure.

Next, an example of a hardware configuration of the information processing apparatus 100 according to the first embodiment of the present disclosure will be described with reference to FIG. 5. FIG. 5 is a block diagram showing a hardware configuration of an information processing apparatus according to an embodiment of the present disclosure. Note that, herein, description will be continued by assuming that the hardware configuration is the hardware configuration of the information processing apparatus 100 according to the first embodiment of the present disclosure will be described. However, this configuration is also applicable to an information processing apparatus 200 according to a second embodiment of the present disclosure and an information processing apparatus 300 according to a third embodiment of the present disclosure.

When referring to FIG. 5, the information processing apparatus 100 includes, for example, a telephone network antenna 817, a call processing unit 819, a GPS antenna 821, a GPS processing unit 823, a Wifi antenna 825, a Wifi processing unit 827, a geomagnetic sensor 829, an acceleration sensor 831, a gyro sensor 833, a central processing unit (CPU) 839, a read only memory (ROM) 841, a random access memory (RAM) 843, an operation unit 847, a display unit 849, a decoder 851, a speaker 853, an encoder 855, a microphone 857, and a storage unit 859. The information processing apparatus 100 may be, for example, a smartphone.

(Telephone Network Antenna 817)

The telephone network antenna 817 is an example of an antenna having a function of wirelessly connecting to a mobile phone network for calling and communication. The telephone network antenna 817 can supply a call signal received via the mobile phone network to the call processing unit 819.

(Call Processing Unit 819)

The call processing unit 819 has a function of performing various kinds of signal processing with respect to signals transmitted/received by the telephone network antenna 817. The call processing unit 819 can perform various kinds of signal processing with respect to, for example, an audio signal that has been input via the microphone 857 and has been encoded by the encoder 855 and supply the audio signal to the telephone network antenna 817. Further, the call processing unit 819 can perform various kinds of signal processing with respect to an audio signal supplied from the telephone network antenna 817 and supply the audio signal to the decoder 851.

(GPS Antenna 821)

The GPS antenna 821 is an example of an antenna for receiving a signal from a positioning satellite. The GPS antenna 821 can receive GPS signals from a plurality of GPS satellites and inputs the received GPS signals to the GPS processing unit 823.

(GPS Processing Unit 823)

The GPS processing unit 823 is an example of a calculation unit for calculating position information on the basis of signals received from the positioning satellites. The GPS processing unit 823 calculates current position information on the basis of a plurality of GPS signals input from the GPS antenna 821 and outputs the calculated position information. Specifically, the GPS processing unit 823 calculates a position of each GPS satellite on the basis of orbit data of the GPS satellites and calculates a distance between each GPS satellite and the information processing apparatus 100 on the basis of a differential time between a transmission time and a receiving time of a GPS signal. Then, it is possible to calculate a current three-dimensional position on the basis of the calculated position of each GPS satellite and the distance between each GPS satellite and the information processing apparatus 100. Note that the orbit data of the GPS satellite used herein may be included in, for example, a GPS signal. Alternatively, the orbit data of the GPS satellite may be acquired from an external server via the communication antenna 825.

(Wifi Antenna 825)

The Wifi antenna 825 is an antenna having a function of transmitting/receiving a communication signal to/from a wireless local area network (LAN) communication network in accordance with, for example, specifications of Wifi. The Wifi antenna 825 can supply the received signal to the Wifi processing unit 827.

(Wifi Processing Unit 827)

The Wifi processing unit 827 has a function of performing various kinds of signal processing with respect to a signal supplied from the Wifi antenna 825. The Wifi processing unit 827 can supply a digital signal generated from the supplied analog signal to the CPU 839.

(Geomagnetic Sensor 829)

The geomagnetic sensor 829 is a sensor for detecting geomagnetism as a voltage value. The geomagnetic sensor 829 may be a three-axis geomagnetic sensor for detecting geomagnetism in an X-axis direction, in a Y-axis direction, and in a Z-axis direction. The geomagnetic sensor 829 can supply data of the detected geomagnetism to the CPU 839.

(Acceleration Sensor 831)

The acceleration sensor 831 is a sensor for detecting acceleration as a voltage value. The acceleration sensor 831 may be a three-axis acceleration sensor for detecting acceleration along the X-axis direction, acceleration along the Y-axis direction, and acceleration along the Z-axis direction. The acceleration sensor 831 can supply data of the detected acceleration to the CPU 839.

(Gyro Sensor 833)

The gyro sensor 833 is a kind of measuring instrument for detecting an angle and an angular velocity of an object. This gyro sensor 833 may be a three-axis gyro sensor for detecting speed (angular velocity) at which a rotation angle changes around the X axis, the Y axis, and the Z axis as a voltage value. The gyro sensor 833 can supply data of the detected angular velocity to the CPU 839.

(CPU 839)

The CPU 839 functions as an arithmetic processing unit and a control device and controls the whole operation in the information processing apparatus 100 in accordance with various programs. Further, the CPU 839 may be a microprocessor. This CPU 839 can realize various functions in accordance with the various programs.

(ROM 841, RAM 843)

The ROM 841 can store programs used by the CPU 839, operation parameters, and the like. The RAM 843 can temporarily store programs used in execution of the CPU 839, parameters appropriately changed in execution thereof, and the like.

(Operation Unit 847)

The operation unit 847 has a function of generating an input signal for allowing the user to perform desired operation. The operation unit 847 may be made up of, for example, an input unit for allowing the user to input information, such as a touch sensor, a mouse, a keyboard, a button, a microphone, a switch, and a lever, and an input control circuit for generating an input signal on the basis of input by the user and outputting the input signal to the CPU 839.

(Display Unit 849)

The display unit 849 is an example of an output device and may be a display device such as a liquid crystal display (LCD) device or an organic light emitting diode (OLED) display device. The display unit 849 can provide information to the user by displaying a screen.

(Decoder 851, Speaker 853)

The decoder 851 has a function of performing decoding, analog conversion, and the like of input data in accordance with control by the CPU 839. The decoder 851 can perform decoding, analog conversion, and the like of, for example, audio data input via the telephone network antenna 817 and the call processing unit 819 and output an audio signal to the speaker 853. Further, the decoder 851 can perform decoding, analog conversion, and the like of, for example, audio data input via the Wifi antenna 825 and the Wifi processing unit 827 and output an audio signal to the speaker 853. The speaker 853 can output audio on the basis of the audio signal supplied from the decoder 851.

(Encoder 855, Microphone 857)

The encoder 855 has a function of performing digital conversion, encoding, and the like of input data in accordance with control by the CPU 839. The encoder 855 can perform digital conversion, encoding, and the like of an audio signal input from the microphone 857 and output audio data. The microphone 857 can collect audio and output the audio as an audio signal.

(Storage Unit 859)

The storage unit 859 is a device for storing data and can include a storage medium, a recording device for recording data on the storage medium, a reading device for reading data from the storage medium, a deletion device for deleting data recorded on the storage medium, and the like. Herein, the storage medium may be, for example, a nonvolatile memory such as a flash memory, a magnetoresistive random access memory (MRAM), a ferroelectric random access memory (FeRAM), a phase change random access memory (PRAM), and an electronically erasable and programmable read only memory (EEPROM) or a magnetic storage medium such as a hard disk drive (HDD). This storage unit 859 can store a correspondence table.

2-3. Operation Example

Figure 6:
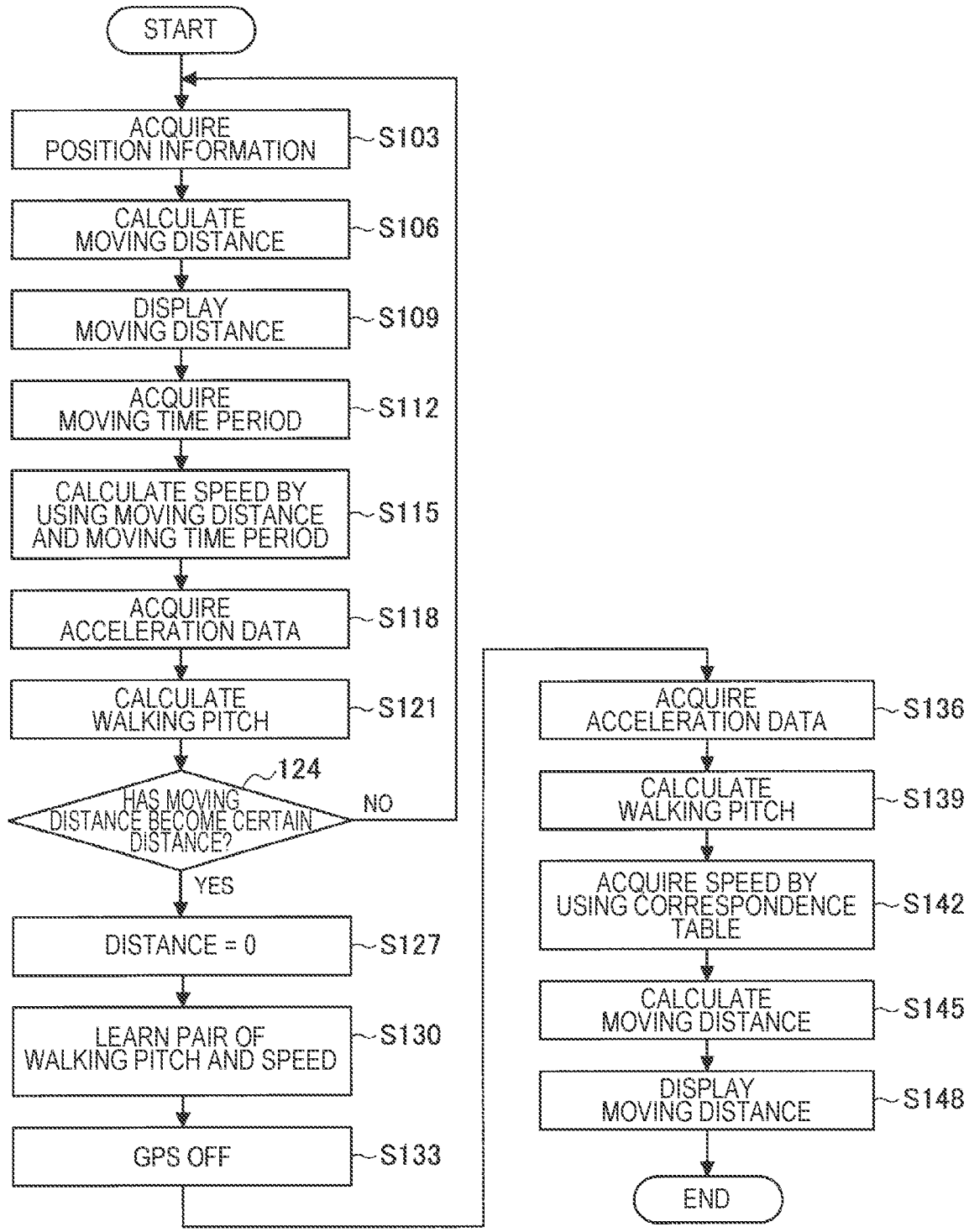
FIG. 6 is a flowchart showing an example of operation of the information processing apparatus according to the first embodiment of the present disclosure.

Next, operation of the information processing apparatus 100 according to the first embodiment of the present disclosure will be described with reference to FIG. 6. FIG. 6 is a flowchart showing an example of the operation of the information processing apparatus 100 according to the first embodiment of the present disclosure.

First, the information processing apparatus 100 causes the absolute positioning unit 101 to acquire position information (S103).

Next, the distance calculation unit 102 calculates a current moving distance of a user on the basis of the position information acquired by the absolute positioning unit 101 (S106).

Then, the information processing apparatus 100 displays the calculated moving distance on the display unit 849 to notify the user of the calculated moving distance (S109). Calculation and display of the moving distance are continuously performed in real time, and therefore the user can grasp a current running distance while running Next, the information processing apparatus 100 acquires a moving time period until a current time measured by a counting unit (not shown) (S112) and calculates a current moving speed of the user by using the moving time period and the calculated moving distance (S115).

Then, the walking pitch calculation unit 104 acquires acceleration data from the acceleration sensor 831 (S118) and calculates a current walking pitch of the user on the basis of the acceleration data (S121).

Next, S103 to S121 described above are repeated until the moving distance of the user becomes a certain distance (for example, 100 m) (S124). Note that the calculated speed and walking pitch can be temporarily stored on the storage unit 859.

Then, in a case where the moving distance of the user becomes the certain distance (S124/Yes), a measured distance is reset to 0 (S127).

Then, the learning unit 106 learns a pair between the walking pitch and the speed. For example, the learning unit 106 calculates an average value of the walking pitch and an average value of the speed on the basis of the above walking pitch and speed that have been continuously and temporarily stored until the moving distance becomes the certain distance, generates a correspondence table of the average values, and stores the correspondence table on the correspondence table storage unit 107 (S130).

Next, the on/off control unit 105 performs control to turn off the absolute positioning unit 101 (for example, GPS) (S133).

Then, the walking pitch calculation unit 104 acquires acceleration data (S136) and calculates a current walking pitch of the user when the GPS is off (S139).

Next, the speed acquisition unit 108 refers to the correspondence table stored on the correspondence table storage unit 107 on the basis of the calculated walking pitch and acquires a current speed of the user (S142).

Then, the autonomous distance calculation unit 109 calculates a current moving distance of the user on the basis of the acquired speed (S145).

Then, the information processing apparatus 100 displays the calculated moving distance on the display unit 849 (S148).

As described above, in the present embodiment, even in a case where the GPS is controlled to be off and an absolute position of the user cannot be acquired, it is possible to calculate a moving distance of the user by using a learning result of a correspondence table showing a correlation between speed and walking pitch and present the moving distance to the user. Further, learning of the correspondence table is performed by using a certain distance based on accuracy of the GPS as a threshold, and therefore it is possible to perform GPS operation necessary and sufficient to secure learning accuracy.

2-4. Modification Example

Operation processing according to the present embodiment is not limited to the flow shown in FIG. 6 and, for example, the GPS may be controlled to be turned on again. Hereinafter, specific description will be provided with reference to FIGS. 7 and 8.

Figure 7:
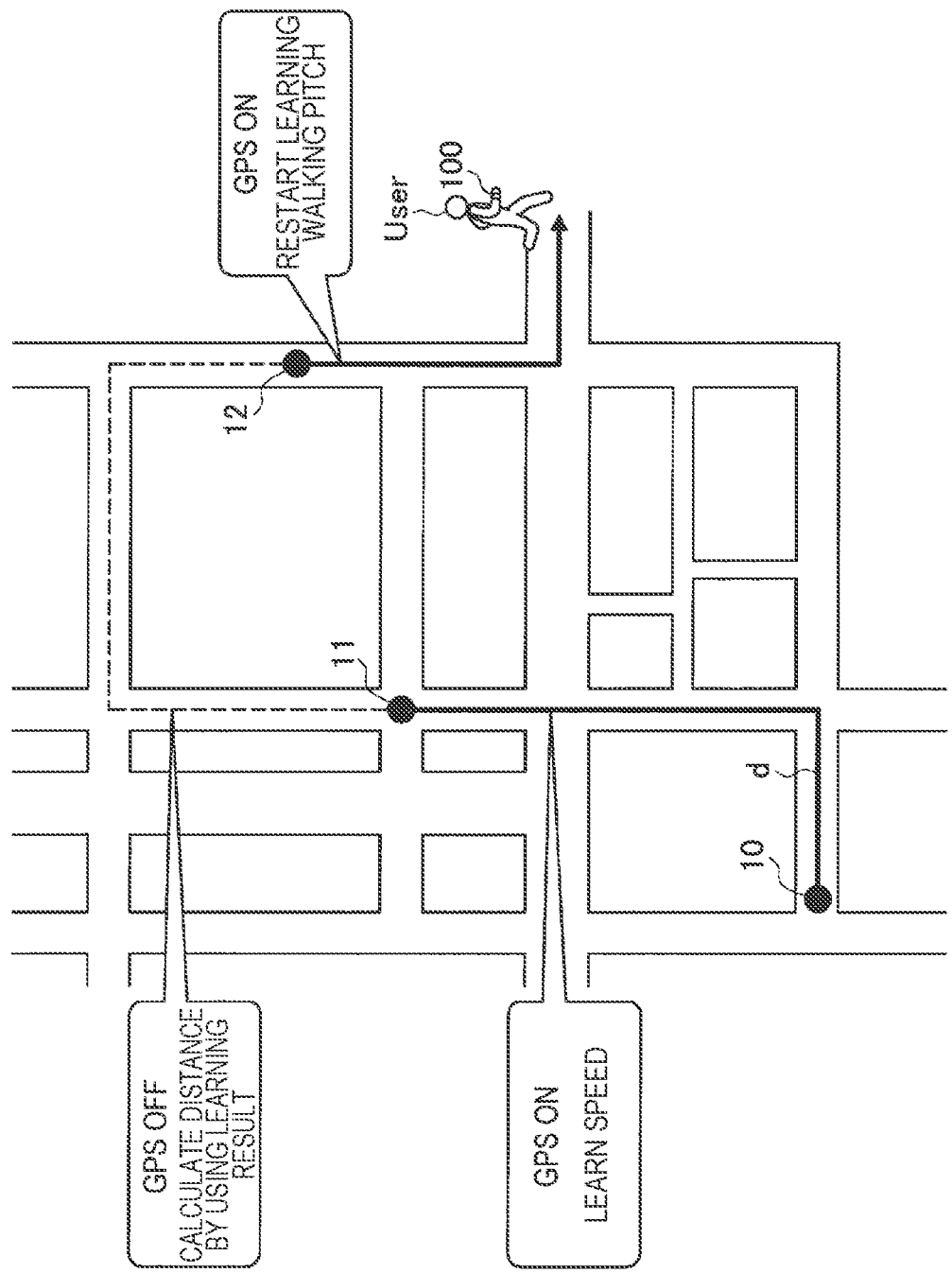
FIG. 7 is a view for describing a control system according to a modification example of the first embodiment.

FIG. 7 is a view for describing a control system according to a modification example of the first embodiment. As shown in FIG. 7, for example, in a case where the user is running while carrying the information processing apparatus 100, operation similar to the operation in the first embodiment that has been described with reference to FIG. 1 is performed from the start spot 10 to a moving spot 12. That is, the GPS provided in the information processing apparatus 100 is controlled to be on from the start spot 10 to the movement spot 11 located at the certain distance d therefrom, and a distance is calculated on the basis of position information acquired by the GPS, and, in addition, learning of a walking pitch is performed during this time. Then, the GPS is controlled to be off from the movement spot 11 by using the user having moved the certain distance d as a trigger, and a moving distance is calculated on the basis of, for example, a walking pitch acquired by the acceleration sensor 831 and a learning result that has been obtained while the GPS has been controlled to be on.

In the present modification example, the GPS is controlled to be turned on again at the moving spot 12, and therefore it is possible to restart distance calculation based on position information acquired by the GPS and learning of a walking pitch. A condition of restart of learning is, for example, a case where a change in walking pitch of the user from a walking pitch obtained at the time of the previous learning is equal to or greater than a certain level. This embodiment learns a correlation between walking pitch and speed, and therefore a change in walking pitch is preferably used as a trigger.

Figure 8:
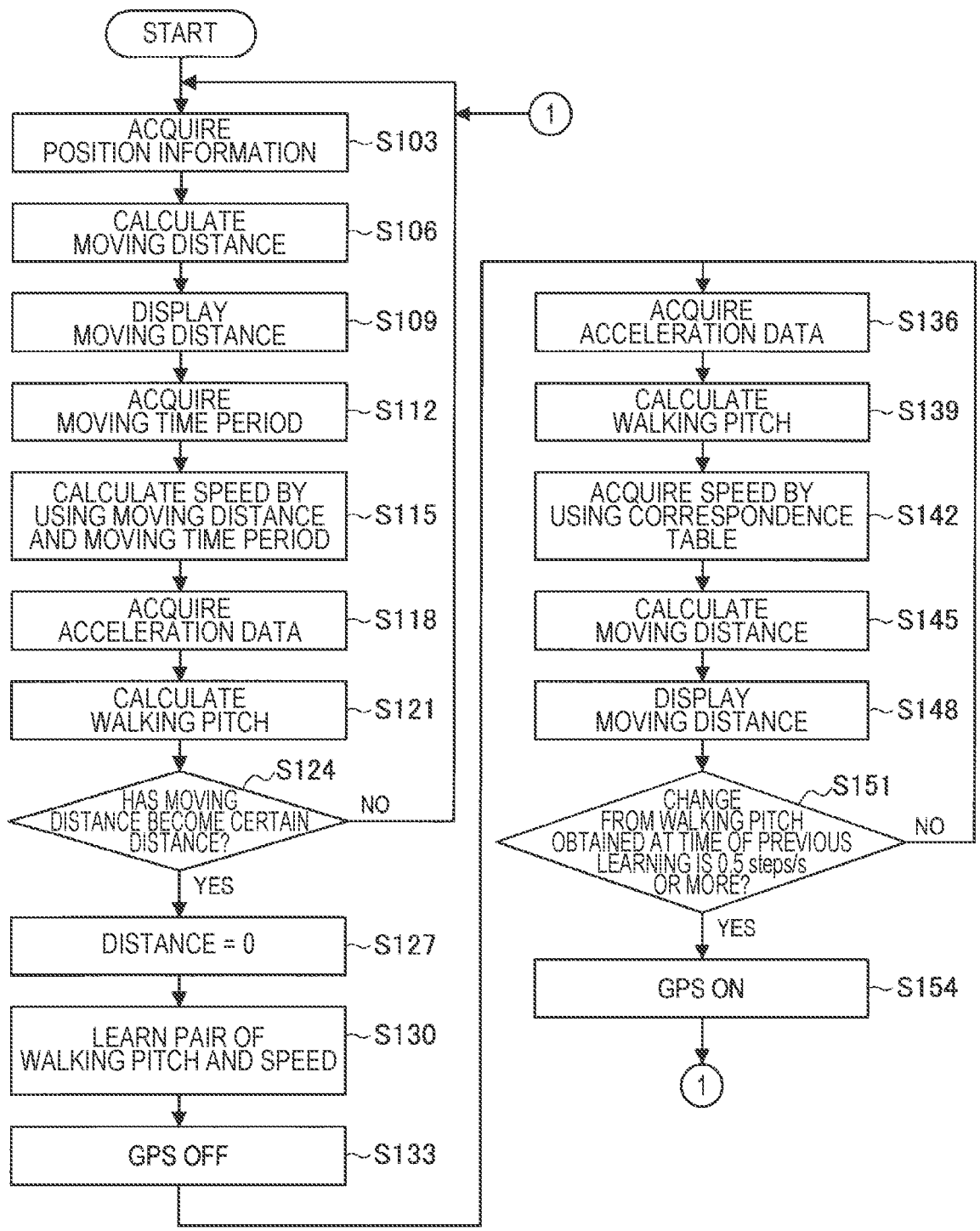
FIG. 8 is a flowchart showing an example of operation of an information processing apparatus according to the modification example of the first embodiment of the present disclosure.

Next, operation processing of the present modification example will be described with reference to FIG. 8. FIG. 8 is a flowchart showing an example of operation of the information processing apparatus 100 according to the modification example of the first embodiment of the present disclosure.

In S103 to S148 in FIG. 8, processing similar to the processing in the steps in the first embodiment that has been described with reference to FIG. 6 is performed. That is, the information processing apparatus 100 performs position measurement using the GPS (an example of the absolute positioning unit 101), calculation of a moving distance, and learning of a walking pitch and speed until the moving distance of the user becomes a certain distance and turns off the GPS when the moving distance becomes the certain distance. When the GPS is turned off, the information processing apparatus 100 calculates a moving distance of the user by using a current walking pitch acquired by the acceleration sensor 831 and speed acquired by the autonomous distance calculation unit 109 referring to a correspondence table (learning result).

In a case where a change in walking pitch of the user from a walking pitch obtained at the time of previous learning is a predetermined value (for example, 0.5 steps/s) or more (S151/Yes), the information processing apparatus 100 according to the present modification example turns on the GPS again (S154) and restarts position measurement using the GPS, calculation of a moving distance, and learning of the walking pitch and the speed (S103 to S130). Then, in a case where the change in the walking pitch is less than the predetermined value (S151/No), the information processing apparatus 100 returns to step S136.

As described above, in the present modification example, it is possible to repeat turning on the GPS and restarting learning and turning off the GPS and stopping learning. Note that, regarding display of a moving distance obtained in a case where the GPS is on in S112, in a case where, for example, it is determined that a GPS error is large (for example, a case where GPS accuracy is reduced, such as a place where a reception strength is weak), the information processing apparatus 100 may display a moving distance calculated by using a learning result.

3. Second Embodiment

In the first embodiment described above, correspondence (pair) between a walking pitch and speed is learned, and, in a case where the GPS is off, speed is acquired in accordance with a current walking pitch on the basis of a learning result and a current moving distance is calculated. However, learning according to the present embodiment is not limited thereto. For example, the control system according to the present disclosure may learn correspondence (pair) between a step length and a walking pitch, acquire speed on the basis of the step length and the walking pitch, and calculate a moving distance. Hereinafter, specific description will be provided with reference to FIG. 9.

Figure 9:
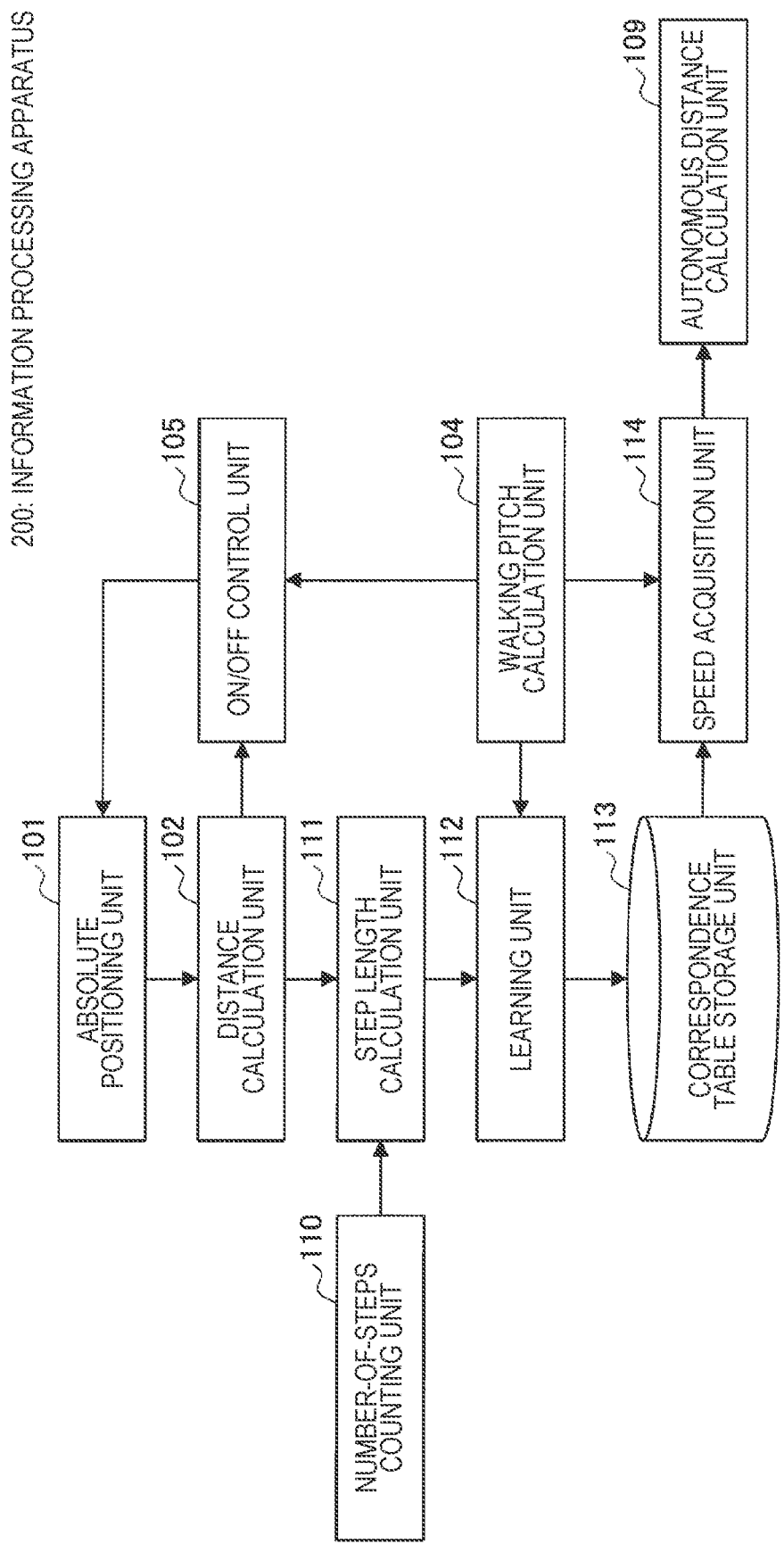
FIG. 9 is a block diagram showing a functional configuration of an information processing apparatus according to a second embodiment of the present disclosure.

FIG. 9 is a block diagram showing a functional configuration of the information processing apparatus 200 according to the second embodiment of the present disclosure. As shown in FIG. 9, the information processing apparatus 200 mainly includes the absolute positioning unit 101, the distance calculation unit 102, the walking pitch calculation unit 104, the on/off control unit 105, a number-of-steps counting unit 110, a step length calculation unit 111, a learning unit 112, a correspondence table storage unit 113, a speed acquisition unit 114, and the autonomous distance calculation unit 109. Description of functional configurations having the same signs as those of the functional configurations in the information processing apparatus 100 according to the first embodiment which has been described with reference to FIG. 3 is herein omitted.

(Number-of-Steps Counting Unit 110)

The number-of-steps counting unit 110 has a function of counting the number of steps of a user. Counting of the number of steps is performed on the basis of, for example, acceleration data detected by the acceleration sensor 831. Further, counting of the number of steps is not limited to the acceleration data and may be performed on the basis of, for example, gyro data detected by a gyro sensor or pressure data detected by a pressure sensor provided in a sole of a shoe.

(Step Length Calculation Unit 111)

The step length calculation unit 111 has a function of calculating a step length of the user. The step length calculation unit 111 can calculate a step length of the user by dividing a moving distance calculated in the distance calculation unit 102 by the number of steps counted in the number-of-steps counting unit 110. For example, the step length calculation unit 111 can determine that the user has moved on the basis of an absolute position acquired by the absolute positioning unit 101 and, every time when the user moves a predetermined distance, acquire the number of steps during that time from the number-of-steps counting unit 110, and calculate a step length. Further, the step length calculation unit 111 outputs the calculated step length to the learning unit 112.

(Learning Unit 112)

The learning unit 112 has a function of learning correspondence (pair) between the step length calculated by the step length calculation unit 111 and a walking pitch calculated by the walking pitch calculation unit 104 while the absolute positioning unit 101 is on. At this time, the learning unit 112 may calculate an average walking pace and associate the average walking pace with the step length. Further, the learning unit 112 can generate a correspondence table of the step length and the walking pitch and store the correspondence table on the correspondence table storage unit 113.

(Correspondence Table Storage Unit 113)

The correspondence table storage unit 113 has a function of storing the correspondence table generated by the learning unit 112. The correspondence table is, for example, information in which the step length (m/step) of the user calculated by the step length calculation unit 111 and a walking pitch (step/s) obtained when the step length is calculated are associated with each other.

(Speed Acquisition Unit 114)

The speed acquisition unit 114 has a function of, in a case where the absolute positioning unit 101 is off, referring to a step length correspondence table stored on the correspondence table storage unit 113 on the basis of a current walking pitch calculated by the walking pitch calculation unit 104, acquiring a corresponding step length, and multiplying the step length by the walking pitch, thereby acquiring a current speed (step length [m/step]×pitch [step/s]=speed [m/s]).

Then, the autonomous distance calculation unit 109 can calculate a moving distance of the user by using the speed acquired by the speed acquisition unit 114.

As described above, the information processing apparatus 200 according to the second embodiment learns a step length and a walking pitch while the GPS is on. Further, in a case where the GPS is turned off, the information processing apparatus 200 can acquire a current walking pitch by using acceleration data, further acquire a corresponding step length from the step length correspondence table, and calculate a moving distance on the basis of the walking pitch and the step length. Note that an on/off control timing of the GPS can be performed in the same way as the first embodiment that has been described with reference to FIGS. 6 and 8.

4. Third Embodiment

In the above-mentioned first and second embodiments, the following has been described: in a marathon application, a walking application, or the like, even in a case where the GPS is turned off, a moving distance of the user can be autonomously calculated by using a learning result obtained when the GPS is on. However, the control system according to the present disclosure is not limited thereto. For example, even in a case where the GPS is turned off, the control system according to the present disclosure can also perform autonomous positioning of a current position of the user by using a learning result obtained when the GPS is on. Hereinafter, specific description will be provided with reference to FIG. 10.

4-1. Functional Configuration Example

Figure 10:
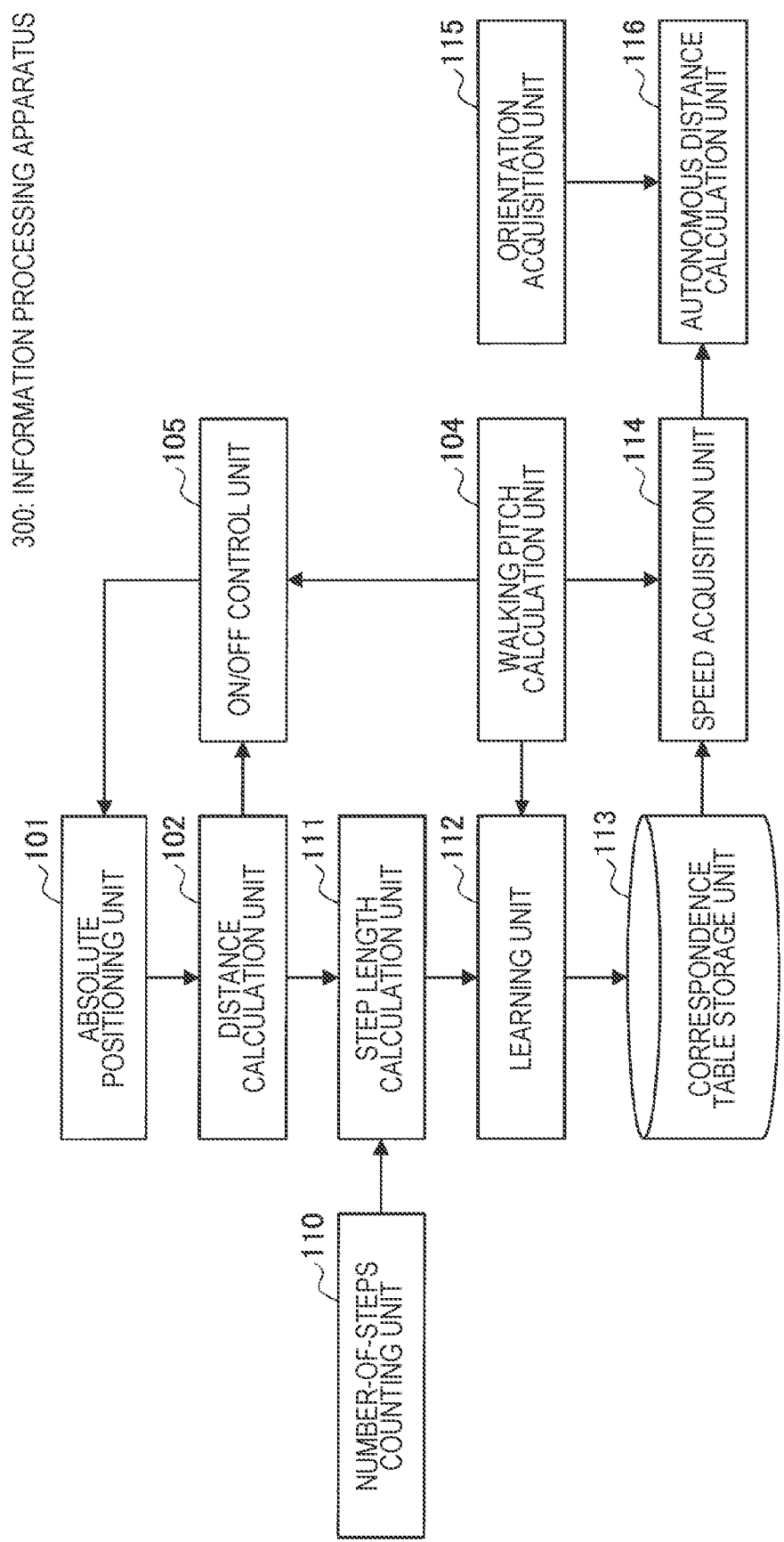
FIG. 10 is a block diagram showing a functional configuration of an information processing apparatus according to a third embodiment of the present disclosure.

FIG. 10 is a block diagram showing a functional configuration of the information processing apparatus 300 according to the third embodiment of the present disclosure. As shown in FIG. 10, the information processing apparatus 300 mainly includes the absolute positioning unit 101, the distance calculation unit 102, the walking pitch calculation unit 104, the on/off control unit 105, the number-of-steps counting unit 110, the step length calculation unit 111, the learning unit 112, the correspondence table storage unit 113, the speed acquisition unit 114, an orientation acquisition unit 115, and an autonomous positioning unit 116. Description of functional configurations having the same signs as those of the functional configurations in the information processing apparatus 100 according to the first embodiment which has been described with reference to FIG. 3 and the functional configurations in the information processing apparatus 200 according to the second embodiment which has been described with reference to FIG. 9 is herein omitted.

(Orientation Acquisition Unit 115)

The orientation acquisition unit 115 has a function of acquiring information on an orientation in which the user progresses. For example, the orientation acquisition unit 115 may use the geomagnetic sensor 829.

(Autonomous Positioning Unit 116)

The autonomous positioning unit 116 has a function of acquiring current position information by calculating a relative position on the basis of information acquired by a sensor or the like. The autonomous positioning unit 116 is realized by, for example, pedestrian dead-reckoning (PDR).

The autonomous positioning unit 116 can calculate a relative position from a specified spot on the basis of the orientation in which the user progresses and a moving speed and set a spot moved from the specified spot by a distance from the relative position as current position information. Herein, the specified spot may be, for example, a spot where the absolute positioning unit 101 has finally acquired an absolute position. Specifically, the autonomous positioning unit 116 acquires current position information by calculating a relative position on the basis of the orientation in which the user progresses acquired by the orientation acquisition unit 115 and the moving speed acquired by the speed acquisition unit 114. Note that the speed acquisition unit 114 can calculate the moving speed by multiplying a current walking pitch of the user acquired by the walking pitch calculation unit 104 by a corresponding step length acquired from the correspondence table of the walking pitch and the step length stored on the correspondence table storage unit 113.

4-2. Operation Example

Figure 11:
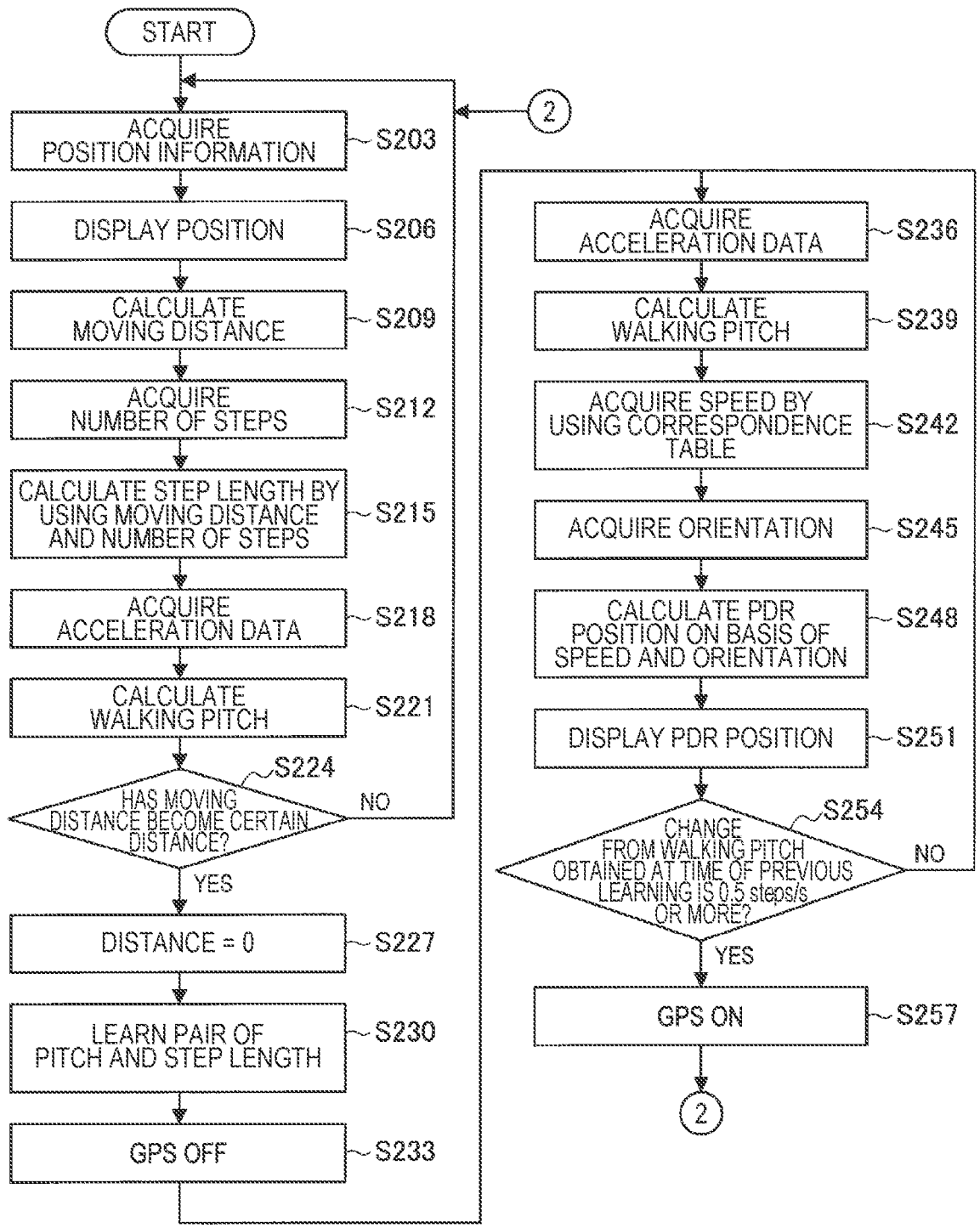
FIG. 11 is a flowchart showing an example of operation of the information processing apparatus according to the third embodiment of the present disclosure.

Next, an operation example according to the present embodiment will be described with reference to FIG. 11. FIG. 11 is a flowchart showing an example of operation of the information processing apparatus 300 according to the third embodiment of the present disclosure.

First, the information processing apparatus 300 causes the absolute positioning unit 101 to acquire position information (S203), displays the acquired current position on the display unit 849 to notify a user of the acquired current position (S206).

Next, the distance calculation unit 102 calculates a current moving distance of the user on the basis of the position information acquired by the absolute positioning unit 101 (S209).

Then, the information processing apparatus 300 causes the number-of-steps counting unit 110 to acquire the number of steps of the user (S212).

Next, the information processing apparatus 300 causes the step length calculation unit 111 to calculate a step length of the user on the basis of the moving distance of the user calculated by the distance calculation unit 102 and the number of steps of the user counted through the moving distance by the number-of-steps counting unit 110 (S215).

Then, the information processing apparatus 300 acquires acceleration data from the acceleration sensor 831 (S218) and causes the walking pitch calculation unit 104 to calculate a walking pitch (S221).

Next, S203 to S221 described above are repeated until the moving distance of the user becomes a certain distance (for example, 100 m) (S224). Note that the calculated step length and walking pitch can be temporarily stored on the storage unit 859.

Then, in a case where the moving distance of the user becomes the certain distance (S224/Yes), a measured distance is reset to 0 (S227).

Then, the learning unit 112 learns a pair between the walking pitch and the step length. For example, the learning unit 112 calculates an average value of the walking pitch and an average value of the step length on the basis of the above walking pitch and step length that have been continuously and temporarily stored until the moving distance becomes the certain distance, generates a correspondence table of the average values, and stores the correspondence table on the correspondence table storage unit 113 (S230).

Next, the on/off control unit 105 performs control to turn off the absolute positioning unit 101 (for example, GPS) (S233).

Then, the walking pitch calculation unit 104 acquires acceleration data (S236) and calculates a current walking pitch of the user when the GPS is off (S239).

Next, the speed acquisition unit 114 refers to the correspondence table stored on the correspondence table storage unit 113 on the basis of the calculated walking pitch and acquires a current speed of the user (S242). Specifically, the speed acquisition unit 114 calculates a moving speed by multiplying the current walking pitch by a corresponding step length acquired by referring to the correspondence table.

Then, the orientation acquisition unit 115 calculates a current moving direction (i.e., orientation) of the user on the basis of, for example, geomagnetic data detected by the geomagnetic sensor 829 (S245).

Then, the autonomous positioning unit 116 calculates a current position (also referred to as "PDR position") of the user on the basis of the acquired speed and orientation (S248).

Then, the information processing apparatus 300 displays the calculated PDR position on the display unit 849 (S251).

In a case where a change in walking pitch of the user from a walking pitch obtained at the time of previous learning is a predetermined value (for example, 0.5 steps/s) or more (S254/Yes), the information processing apparatus 300 turns on the GPS again (S257) and restarts position measurement using the GPS and learning of the walking pitch and the step length (S203 to S230). Further, in a case where the change in the walking pitch is less than the predetermined value (S254/No), the information processing apparatus 300 returns to step S236.

As described above, the present embodiment is not limited to autonomous calculation of a moving distance using a learning result, and it is possible to perform absolute positioning operation necessary and sufficient to secure learning accuracy by turning off absolute positioning using GPS or the like in accordance with a moving distance also in a case where autonomous positioning of a current position using a learning result is performed. With this, it is possible to minimize absolute positioning operation to thereby cut power consumption and secure learning accuracy to thereby continue highly accurate autonomous positioning for a long time. Note that, regarding display of a current position (GPS position) obtained in a case where the GPS is on in S206, in a case where, for example, it is determined that a GPS error is large (for example, a case where GPS accuracy is reduced such as a place where a reception strength is weak), the information processing apparatus 300 may display a PDR position obtained by performing autonomous positioning by using a learning result. Further, a value obtained by giving predetermined weighting to the GPS position and predetermined weighting to the PDR position and adding the weighted GPS position and the weighted PDR position may be displayed as a current position.

5. Conclusion

As described above, in the information process systems according to the embodiments of the present disclosure, it is possible to improve accuracy of autonomous positioning by turning off absolute positioning in accordance with a moving distance.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, it is also possible to create a computer program for causing a hardware such as a CPU, a ROM, and a RAM, which are embedded in the above described information processing apparatuses 100, 200 and 300, to execute the above-described functions of the information processing apparatuses 100, 200 and 300. Moreover, it may be possible to provide a computer-readable recording medium having the computer program stored therein.

Further, the control system according to the present embodiment may be such that at least part of functions of the information processing apparatus 100, 200, or 300 exists in a server (cloud) and the information processing apparatus 100, 200, or 300 and the server transmit/receive data. In this case, for example, the server may include the distance calculation unit 102, the speed calculation unit 103, the walking pitch calculation unit 104, the on/off control unit 105, the learning unit 106, the correspondence table storage unit 107, the speed acquisition unit 108, and the autonomous distance calculation unit 109. The server receives an absolute position of a user measured by the absolute positioning unit 101 provided in the information processing apparatus 100 and performs distance calculation, speed calculation, and learning. Further, the server receives acceleration data detected by the acceleration sensor 831 provided in the information processing apparatus 100, autonomously calculates a distance by using a learned correspondence table, and returns a calculation result to the information processing apparatus 100.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:

a distance calculation unit configured to calculate a moving distance of a user by using an absolute position of the user measured by an absolute positioning unit; and a control unit configured to perform control to turn off the absolute positioning unit in a case where the moving distance becomes a predetermined distance.

(2)

The information processing apparatus according to (1), further including:

a speed calculation unit configured to calculate a moving speed of the user on the basis of the moving distance and a moving time period;

a pitch calculation unit configured to calculate a walking pitch of the user on the basis of the moving time period and the number of steps of the user measured by a number-of-steps measurement unit; and a learning unit configured to learn correspondence between the calculated moving speed and the calculated walking pitch while the absolute positioning unit is on.

(3)

The information processing apparatus according to (2), in which the number-of-steps measurement unit measures the number of steps on the basis of acceleration data detected by an acceleration sensor.

(4)

The information processing apparatus according to (2) or (3), in which in a case where the absolute positioning unit is controlled to be turned off, the learning unit stores a correspondence table of the moving speed and the walking pitch on a storage unit as a learning result.

(5)

The information processing apparatus according to (4), further including a speed acquisition unit configured to acquire a current moving speed of the user on the basis of a current walking pitch calculated by the pitch calculation unit while the absolute positioning unit is off and a moving speed corresponding to the walking pitch acquired by referring to the correspondence table in the storage unit.

(6)

The information processing apparatus according to (1), further including:

a step length calculation unit configured to calculate a step length of the user on the basis of the moving distance and the number of steps;

a pitch calculation unit configured to calculate a walking pitch of the user on the basis of a moving time period and the number of steps of the user measured by a number-of-steps measurement unit; and a learning unit configured to learn correspondence between the calculated step length and the calculated walking pitch while the absolute positioning unit is on.

(7)

The information processing apparatus according to (6), in which the number-of-steps measurement unit measures the number of steps on the basis of acceleration data detected by an acceleration sensor.

(8)

The information processing apparatus according to (6) or (7), in which in a case where the absolute positioning unit is controlled to be turned off, the learning unit stores a correspondence table of the step length and the walking pitch on a storage unit as a learning result.

(9)

The information processing apparatus according to (8), further including a speed acquisition unit configured to acquire a current moving speed of the user on the basis of a current walking pitch calculated by the pitch calculation unit while the absolute positioning unit is off and a step length corresponding to the walking pitch acquired by referring to the correspondence table in the storage unit.

(10)

The information processing apparatus according to (5) or (8), further including an autonomous distance calculation unit configured to calculate a moving distance on the basis of the acquired moving speed and a current walking pitch of the user while the absolute positioning unit is off.

(11)

The information processing apparatus according to any one of (5) to (8), further including:

a direction acquisition unit configured to acquire a moving direction of the user; and an autonomous positioning unit configured to calculate a current position of the user on the basis of the acquired moving speed and a current moving direction of the user while the absolute positioning unit is off.

(12)

The information processing apparatus according to any one of (2) to (11), in which in a case where, after the control unit performs control to turn off the absolute positioning unit, a change in walking pitch of the user from a walking pitch learned at a previous time is a predetermined value or more, the control unit performs control to turn on the absolute positioning unit.

(13)

The information processing apparatus according to any one of (1) to (12), in which the predetermined distance is determined in accordance with accuracy of the absolute positioning unit.

(14)

An information process method including causing a processor to calculate a moving distance of a user by using an absolute position of the user measured by an absolute positioning unit, and perform control to turn off the absolute positioning unit in a case where the moving distance becomes a predetermined distance.

(15)

A program for causing a computer to function as a distance calculation unit configured to calculate a moving distance of a user by using an absolute position of the user measured by an absolute positioning unit, and a control unit configured to perform control to turn off the absolute positioning unit in a case where the moving distance becomes a predetermined distance.

REFERENCE SIGNS LIST

100, 200, 300 information processing apparatus
101 absolute positioning unit
102 distance calculation unit
103 speed calculation unit
104 walking pitch calculation unit 105 on/off control unit
106 learning unit
107, 113 correspondence table storage unit
108 speed acquisition unit
109 autonomous distance calculation unit
110 number-of-steps counting unit
111 step length calculation unit
112 learning unit
114 speed acquisition unit
115 orientation acquisition unit
116 autonomous positioning unit

The invention claimed is:

1. An information processing apparatus, comprising:
circuitry configured to:
acquire a first number of steps of a user while a Global Positioning System (GPS) is on;
calculate a first walking pitch of the user based on the first number of steps;
acquire an absolute position of the user, wherein the absolute position is measured by the GPS;
calculate a first moving distance of the user based on the absolute position of the user;
control to turn off the GPS based on the first moving distance that is equal to a threshold distance;
acquire a second number of steps of the user while the GPS is turned off;
calculate a second walking pitch of the user based on the second number of steps;
calculate a difference in walking pitch between the second walking pitch and the first walking pitch; and
control, while the GPS is turned off, to turn on the GPS based on the difference in walking pitch that is greater than or equal to a threshold value.

2. The information processing apparatus according to claim 1,
wherein the circuitry is further configured to:
acquire a moving time period of the user;
calculate a first moving speed of the user based on the first moving distance and the moving time period of the user;
calculate the first walking pitch of the user based on the moving time period; and
determine a correspondence between the first moving speed and the first walking pitch while the GPS is on.

3. The information processing apparatus according to claim 2, wherein the circuitry is further configured to measure each of the first number of steps and the second number of steps based on acceleration data detected by an acceleration sensor.

4. The information processing apparatus according to claim 2, wherein the circuitry is further configured to store a correspondence table of the first moving speed and the first walking pitch based on the determined correspondence between the first moving speed and the first walking pitch.

5. The information processing apparatus according to claim 4, wherein
the circuitry is further configured to acquire a second moving speed of the user based on the correspondence table, and
the second moving speed corresponds to the second walking pitch.

6. The information processing apparatus according to claim 5, wherein the circuitry is further configured to calculate, while the GPS is off, a second moving distance based on the second moving speed and the second walking pitch.

7. The information processing apparatus according to claim 5, wherein the circuitry is further configured to:
acquire a moving direction of the user; and
calculate, while the GPS is off, a current position of the user based on the second moving speed and the moving direction.

8. The information processing apparatus according to claim 1, wherein the circuitry is further configured to:
acquire a moving time period of the user;
calculate a first step length of the user based on the first moving distance and the first number of steps;
calculate the first walking pitch of the user based on the moving time period of the user; and
determine a correspondence between the first step length and the first walking pitch while the GPS is on.

9. The information processing apparatus according to claim 8, wherein the circuitry is further configured to measure each of the first number of steps and the second number of steps based on acceleration data detected by an acceleration sensor.

10. The information processing apparatus according to claim 8, wherein the circuitry is further configured to store a correspondence table of the first step length and the first walking pitch based on the determined correspondence between the first step length and the first walking pitch.

11. The information processing apparatus according to claim 10, wherein
the circuitry is further configured to acquire a second step length of the user based on the correspondence table, and
the second step length corresponds to the second walking pitch.

12. An information process method, comprising
acquire a first number of steps of a user while a Global Positioning System (GPS) is on;
calculating a first walking pitch of the user based on the first number of steps;
acquiring an absolute position of the user, wherein the absolute position is measured by the GPS;
calculating a moving distance of the user based on the absolute position of the user;
controlling to turn off the GPS based on the moving distance that is equal to a threshold distance;
acquire a second number of steps of the user while the GPS is turned off;
calculating a second walking pitch of the user based on the second number of steps;
calculating a difference in walking pitch between the second walking pitch and the first walking pitch; and
controlling, while the GPS is turned off, to turn on the GPS based on the difference in walking pitch that is greater than or equal to a threshold value.

13. A non-transitory computer-readable medium having stored thereon, computer executable-instructions that, when executed by a processor, cause the processor to execute operations, the operations comprising:
acquiring a first number of steps of a user while a Global Positioning System (GPS) is on;
calculating a first walking pitch of the user based on the first number of steps;
acquiring an absolute position of the user, wherein the absolute position is measured by the GPS;
calculating a moving distance of the user based on the absolute position of the user;
controlling to turn off the GPS based on the moving distance that is equal to a threshold distance;

acquiring a second number of steps of the user while the GPS is turned off;
calculating a second walking pitch of the user based on the second number of steps;
calculating a difference in walking pitch between the second walking pitch and the first walking pitch; and
controlling, while the GPS is turned off, to turn on the GPS based on the difference in walking pitch that is greater than or equal to a threshold value.

* * * * *